United States Patent
Kadoya et al.

(10) Patent No.: US 12,310,941 B2
(45) Date of Patent: May 27, 2025

(54) AGENT FOR PROTECTION OF BLOOD BRAIN SPINAL CORD BARRIER

(71) Applicant: National University Corporation Hokkaido University, Sapporo (JP)

(72) Inventors: Ken Kadoya, Sapporo (JP); Yuki Suzuki, Sapporo (JP); Akihito Sotome, Sapporo (JP); Katsumi Maenaka, Sapporo (JP); Satoko Otsuguro, Sapporo (JP)

(73) Assignee: National University Corporation Hokkaido University, Hokkaido (JP)

( * ) Notice: Subject to any disclaimer, the term of this patent is extended or adjusted under 35 U.S.C. 154(b) by 73 days.

(21) Appl. No.: 17/642,287

(22) PCT Filed: Jun. 24, 2021

(86) PCT No.: PCT/JP2021/024033
§ 371 (c)(1),
(2) Date: Mar. 11, 2022

(87) PCT Pub. No.: WO2021/261571
PCT Pub. Date: Dec. 30, 2021

(65) Prior Publication Data
US 2023/0106974 A1    Apr. 6, 2023

(30) Foreign Application Priority Data

Jun. 24, 2020 (JP) ................. 2020-109190

(51) Int. Cl.
*A61K 31/29* (2006.01)
*A61K 31/4192* (2006.01)
(Continued)

(52) U.S. Cl.
CPC .......... *A61K 31/29* (2013.01); *A61K 31/4192* (2013.01); *A61K 31/4545* (2013.01); *A61K 31/472* (2013.01); *A61P 39/00* (2018.01)

(58) Field of Classification Search
CPC ............... A61K 2300/00; A61K 31/29; A61K 31/4192; A61K 31/422; A61K 31/4545;
(Continued)

(56) References Cited

U.S. PATENT DOCUMENTS

| 8,410,129 B2 | 4/2013 | Brooks-Korn |
| 2005/0186288 A1 | 8/2005 | Chiou et al. |

(Continued)

FOREIGN PATENT DOCUMENTS

| JP | 63174926 A | 7/1988 |
| JP | 2005533047 A | 11/2005 |

(Continued)

OTHER PUBLICATIONS

Suzuki et al., "A Novel Effect for the Smooth Muscle Relaxant Papaverine: Neuroprotective Effect on Spinal Cord Injury Through the Protection of the Blood Spinal Cord Barrier". The Hokkaido Journal of Orthopaedics and Traumatology, vol. 63 (139th suppl.), p. 17, 1-l-5-2, with machine translation, 6 pages (2021).

(Continued)

*Primary Examiner* — Savitha M Rao
(74) *Attorney, Agent, or Firm* — Buchanan Ingersoll & Rooney PC

(57) ABSTRACT

The present invention relates to an agent for protection of vascular endothelial cells, an agent for protection of blood brain spinal cord barrier, and an agent for protection of central nervous system, containing at least one compound selected from the group consisting of muvritinib, brexpiprazole, papaverine, bismuth-containing compounds, and pharmaceutically acceptable salts thereof. The invention (Continued)

also relates to a pharmaceutical composition for the treatment of diseases associated with blood brain spinal cord barrier disruption, containing at least one compound selected from the group consisting of muvritinib, brexpiprazole, papaverine, bismuth-containing compounds, and pharmaceutically acceptable salts thereof.

14 Claims, 13 Drawing Sheets

(51) Int. Cl.
*A61K 31/4545* (2006.01)
*A61K 31/472* (2006.01)
*A61P 39/00* (2006.01)

(58) Field of Classification Search
CPC .. A61K 31/472; A61K 31/496; A61K 33/245; A61P 39/00; A61P 7/04
See application file for complete search history.

(56) References Cited

U.S. PATENT DOCUMENTS

| | | |
|---|---|---|
| 2007/0259031 A1 | 11/2007 | Bankiewicz et al. |
| 2014/0037547 A1 | 2/2014 | Dostmann et al. |
| 2014/0256820 A1 | 9/2014 | Takata et al. |
| 2015/0272946 A1 | 10/2015 | Sato et al. |
| 2020/0129621 A1 | 4/2020 | Stern et al. |

FOREIGN PATENT DOCUMENTS

| | | | |
|---|---|---|---|
| JP | 2015134732 A | 7/2015 | |
| JP | 2015535211 A | 12/2015 | |
| WO | 03103691 A1 | 12/2003 | |
| WO | 2012081713 A1 | 6/2012 | |
| WO | 2014065437 A1 | 5/2014 | |
| WO | 2019010491 A1 | 1/2019 | |
| WO | 2019123378 A1 | 6/2019 | |

OTHER PUBLICATIONS

Soutome et al., "The Neuroprotective Effect After Spinal Cord Injury Through Maintenance of Blood-Spinal Cord Barrier Function of Papaverine", The Journal of Japanese Orthopaedic Surgical Society, 94(8) p. S1837, 2-7-14, with machine translation (2020).
Takagi et al., "Cilostazol Ameliorates Collagenase-Induced Cerebral Hemorrhage by Protecting the Blood-Brain Barrier", Journal of Cerebral Blood Flow & Metabolism, 37(1);123-139 (2017).
Zhao et al., "Peroxisome Proliferator-Activated Receptor γ Agonist Rosiglitazone Protects Blood-Brain Barrier Integrity Following Diffuse Axonal Injury by Decreasing the Levels of Inflammatory Mediators Through a Caveolin-1-Dependent Pathway", Inflammation, 42(3):841-856 (2019).
Zlokovic et al., "The Blood-Brain Barrier in Health and Chronic Neurodegenerative Disorders", Neuron, 57:178-201 (2008).
Obermeier et al., "Development, Maintenance and Disruption of the Blood-Brain Barrier", Nature Medicine, 19 (12):1584-1596 (2013).
Sweeney et al., "Blood-Brain Barrier: From Physiology to Disease and Back", Physiol. Rev., 99:21-78 (2019).
Yuan et al., "Metallodrug Ranitidine Bismuth Citrate Suppresses SARS-COV-2 Replication and Relieves Virus-Associated Pneumonia in Syrian Hamsters", Nature Microbiology, 5:1439-1448, (2020).
Hong et al., "Glutathione and Multidrug Resistance Protein Transporter Mediate a Self-Propelled Disposal of Bismuth in Human Cells", PNAS, 112(11):3211-3216, (2015).
Horai et al., "Cilostazol Strengthens Barrier Integrity in Brain Endothelial Cells", Cellular and Molecular Neurobiology 33:291-307 (2013).
Chen et al., "FGF21 Protects the Blood-Brain Barrier by Unregulating PPARγ via FGFR1/β-klotho After Traumatic Brain Injury", Journal of Neurotrauma, 35:2091-2103, (2018).
Suzuki et al., "Newly Developed High-Throughput Screening Assay Identifies Berberine as a Potential Drug to Protect Blood-Brain Barrier from Toxic Stresses", Neuroscience 1 page (2018).
Suzuki et al., Drug Repositioning for New CNS Injury Treatment: Targeting on Protection of Blood-Brain Barrier. XIV European Meeting on Glial Cells in Health and Disease, 4 pages (2019).
International Search Report and Written Opinion for International Application No. PCT/JP2021/024033, dated Aug. 24, 2021, 7 pages.
Takata et al., "Metformin Induces Up-Regulation of Blood-Brain Barrier Functions by Activating AMP Activated Protein Kinase in Rat Brain Microvascular Endothellal Cells", Biochemical and Biophysical Research Communications, 433:586-590 (2013).
The Extended European Search Report issued Jun. 10, 2024, by the European Patent Office in corresponding European Patent Application No. 21828655.7-1109. (15 pages).
Sweeney, et al., "Blood-brain barrier breakdown in Alzheimer's disease and other neurodegenerative disorders", Nat Rev Neurol. Mar. 2018 ; 14(3): 133-150. doi:10.1038/nrneurol.2017.188.
Zlokovic, "The Blood-Brain Barrier in Health and Chronic Neurodegenerative Disorders", Neuron, 57, Jan. 24, 2008, 178-201.
Rodriguez-Grande, et al., "Early to Long-Term Alterations of CNS Barriers After Traumatic Brain Injury: Considerations for Drug Development", The AAPS Journal, vol. 19, No. 6, Nov. 2017 1615-1625 DOI: 10.1208/s12248-017-0123-3.
Jiang, et al., "Blood-brain barrier dysfunction and recovery after ischemic stroke", Progress in Neurobiology, 163-164, 2018, 144-171.

AGENT FOR PROTECTION OF BLOOD BRAIN SPINAL CORD BARRIER

CROSS-REFERENCE TO RELATED APPLICATIONS

This application is a U.S. national phase application of International Application No. PCT/JP2021/024033, filed Jun. 24, 2021, claiming the benefit of Japanese Application No. 2020-109190, filed Jun. 24, 2020, the contents of each of which are incorporated herein by their entireties for all purposes.

FIELD

The present invention relates to a blood brain spinal cord barrier protective agent including a compound selected from the group consisting of mubritinib, brexpiprazole, papaverine, a bismuth-containing compound, and pharmaceutically acceptable salts thereof.

BACKGROUND

The blood brain spinal cord barrier (BBSCB) is a blood barrier for the central nervous system (CNS) and has an important function in maintaining homeostasis of the CNS as a barrier that restricts the exchange of cells and substances between blood flow and the CNS tissue. The tight junction between the vascular endothelial cells controls the barrier function of the BBSCB, and pericytes and astrocytes around the vascular endothelial cells support maintenance of the barrier function.

The BBSCB includes the blood-brain barrier (BBB), which is a blood barrier for the brain, and the blood-spinal cord barrier (BSCB), which is a blood barrier for the spinal cord. It has been known that disruption of the BBSCB leads to an increase in its permeability and a leakage of cytotoxic substances and inflammatory cells from the blood into the CNS, resulting in damage of the CNS. This causes and exacerbates various CNS diseases.

For example, in the case of spinal cord injury, after mechanical injury (primary injury) by an external impact, additional tissue damage (secondary injury) occurs due to biological reactions such as hematoma, ischemia, edema, and infiltration of inflammatory cells and cytotoxicity, thereby expanding the injured area. Therefore, suppression of secondary injury is expected to be a therapeutic target for suppressing expansion of the injured area and preventing a deterioration in functional prognosis. Because the disruption of the BBSCB after primary injury contributes to the infiltration of inflammatory cells and cytotoxicity, the prevention of the disruption of the BBSCB has been a therapeutic target for spinal cord injury. Methylprednisolone sodium succinate, the only approved therapeutic agent in Japan for patients in the acute phase of spinal cord injury, is considered to have a suppressive effect for secondary injury; however, its efficacy has been questioned worldwide and thus more effective therapeutic agents are desired.

A drug for protecting the BBSCB can be a therapeutic agent for spinal cord injury that suppresses secondary injury, but there are still no BBSCB protective agent that has been shown to be clinically effective. In basic research, cilostazol (Non Patent Literature 1), metformin (Non Patent Literature 2 and Patent Literature 1), and rosiglitazone (Non Patent Literature 3) have been reported to have protective effects for the BBSCB.

CITATION LIST

Non Patent Literatures

Non Patent Literature 1: Takagi T., et al. J Cereb Blood Flow Metab. 2017; 37(1): 123-139
Non Patent Literature 2: Takata F., et al. Biochem Biophys Res Commun. 2013; 433(4): 586-590
Non Patent Literature 3: Zhao., et al. Inflammation. 2019; 42(3): 841-856

Patent Literature

Patent Literature 1: WO2012/081713

SUMMARY

Technical Problem

An object of the present invention is to provide a BBSCB protective agent that protects the BBSCB from its disruption, and is effective in preventing or treating a disease and a pathological condition accompanied with a BBSCB disorder.

Solution to Problem

The inventors of the present invention have found that mubritinib, brexpiprazole, papaverine, and a bismuth-containing compound have a protective effect for vascular endothelial cells and the BBSCB, and have thus completed the present invention below.

(1) A vascular endothelial cell protective agent including at least one compound selected from the group consisting of mubritinib, brexpiprazole, papaverine, a bismuth-containing compound, and pharmaceutically acceptable salts thereof.

(2) A blood brain spinal cord barrier protective agent including at least one compound selected from the group consisting of mubritinib, brexpiprazole, papaverine, a bismuth-containing compound, and pharmaceutically acceptable salts thereof.

(3) A central nervous system (CNS) protective agent including at least one compound selected from the group consisting of mubritinib, brexpiprazole, papaverine, a bismuth-containing compound, and pharmaceutically acceptable salts thereof.

(4) A pharmaceutical composition for preventing and/or treating a disease accompanied with a blood brain spinal cord barrier disorder, the pharmaceutical composition including at least one compound selected from the group consisting of mubritinib, brexpiprazole, papaverine, a bismuth-containing compound, and pharmaceutically acceptable salts thereof.

(5) The pharmaceutical composition according to (4), wherein the disease accompanied with a blood brain spinal cord barrier disorder is selected from the group consisting of injury, infarction and hemorrhage of central nervous system (CNS), an inflammatory disease of CNS, a degenerative disease of CNS, a symptomatic neurological disease, a spinal cord disorder accompanied with spinal cord degeneration, a drug-induced disorder, an infectious disease, and anaphylaxis.

(6) The pharmaceutical composition according to (4) or (5), wherein the disease accompanied with a blood brain spinal cord barrier disorder is selected from the group consisting of brain injury, spinal cord injury, cerebral infarction, spinal cord infarction, brain hemorrhage, spinal cord hemorrhage, multiple sclerosis, encephalomyelitis, optic neuritis, Alzheimer's disease, Parkinson's disease, amyotrophic lateral sclerosis, dementia, epilepsy, compressive myelopathy, a blood brain spinal cord barrier disorder due to an immunosuppressant, a brain infectious disease, a spinal cord infectious disease, and anaphylaxis.

(7) The pharmaceutical composition according to any one of (4) to (6), wherein the disease accompanied with a blood brain spinal cord barrier disorder is brain injury, spinal cord injury, or compressive myelopathy.

Effect of the Invention

According to the present invention, by protecting the BBSCB from its disruption, a disease and a pathological condition of CNS accompanied with a BBSCB disorder can be prevented or treated. Compounds used in the present invention do not need to permeate the BBSCB in order to exhibit their medicinal effect, and since many of these are existing drugs, they have the advantage that problems such as safety have also been solved.

DESCRIPTION OF EMBODIMENTS

Figure 1:
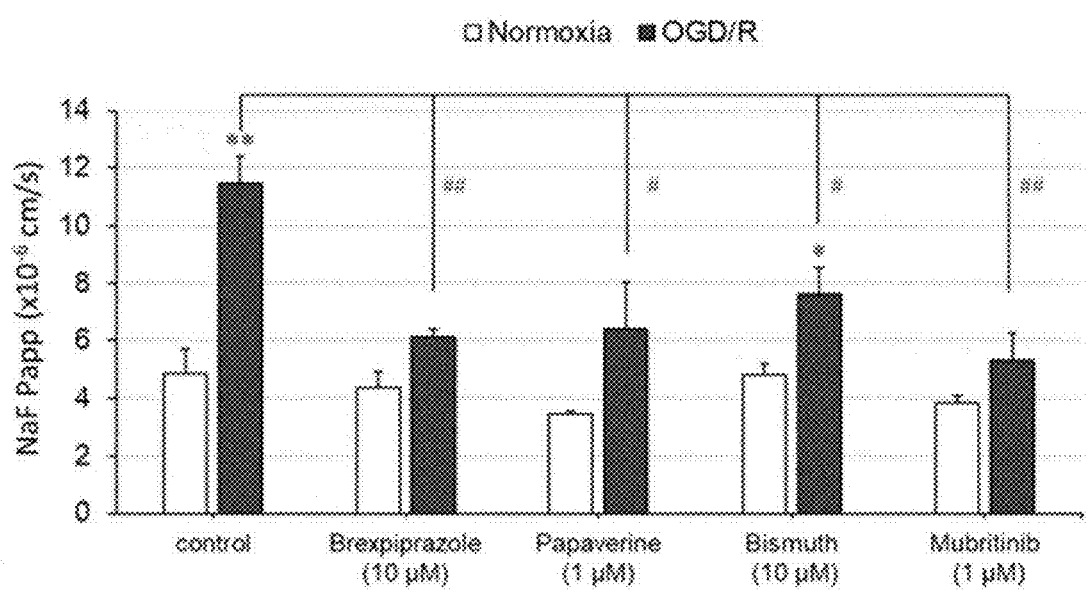
FIG. 1 is a graph of the permeability of sodium fluorescein (Na—F) in a monolayer culture model of rat brain vascular endothelial cells after being subjected to oxygen-glucose deprivation/reoxygenation in the presence of papaverine, mubritinib, brexpiprazole, or bismuth subnitrate.

Mubritinib (IUPAC name: 4-[[4-[4-(triazol-1-yl)butyl]phenoxy]methyl]-2-[(E)-2-[4-(trifluoromethyl)phenyl]ethenyl]-1,3-oxazole, CAS registration number 366017-09-6) is a receptor tyrosine kinase inhibitor having a selective tyrosine kinase inhibitory effect on human epidermal growth factor receptor type 2 (HER2).

Brexpiprazole (IUPAC name: 7-[4-[4-(1-benzothiophen-4-yl)piperazin-1-yl]butoxy]-1H-quinolin-2-one, CAS registration number 913611-97-9) is a drug called a serotonin-dopamine activity modulator (SDAM) that acts as a partial agonist for a dopamine D2 receptor and a serotonin 5-HT1A receptor and as an antagonist for serotonin 5-HT2A receptor, and is used as a therapeutic agent for schizophrenia.

Papaverine (IUPAC name: 1-[(3,4-dimethoxyphenyl) methyl]-6,7-dimethoxyisoquinoline, CAS registration number 58-74-2) is an isoquinoline-based natural alkaloid having a relaxing effect on smooth muscle, and is used as a medicament for improving a convulsive symptom in visceral smooth muscle, and vasodilatation and symptoms in acute arterial embolism, acute pulmonary embolism, peripheral circulation disorder, and coronary circulation disorder.

The bismuth-containing compound is a compound that can be administered as a medicine to a living organism, particularly a human, and has bismuth as a constituent atom, for example, a pharmaceutically acceptable bismuth complex. Bismuth is less toxic compared with arsenic and antimony, which belong to the same family in the periodic table, and various bismuth-containing compounds are used as a bulk pharmaceutical such as an antiflatulent, an antacid, and an astringent. Examples of the bismuth-containing compound that can be used in the present invention include bismuth subnitrate, bismuth subcitrate, bismuth subsalicylate, ranitidine bismuth citrate, bismuth subgallate, bismuth subcarbonate, bismuth aluminate, bismuth carbonate, bismuth citrate, bismuth nitrate, bismuth salicylate, and bismuth tartrate. The bismuth-containing compound is preferably one or more compounds selected from the group consisting of bismuth subnitrate, bismuth subcitrate, bismuth subsalicylate, ranitidine bismuth citrate, bismuth subgallate, and bismuth subcarbonate. The bismuth-containing compound is more preferably bismuth subnitrate, bismuth subcitrate, or bismuth tartrate.

The pharmaceutically acceptable salts of the above four compounds can be an acid addition salt or a base addition salt. Examples of the acid addition salt include an inorganic acid salt such as a hydrochloride, a hydrobromide, a sulfate, a hydroiodide, a nitrate, and a phosphate, and an organic acid salt such as a citrate, an oxalate, an acetate, a formate, a propionate, a benzoate, a trifluoroacetate, a maleate, a tartrate, a methanesulfonate, a benzenesulfonate, and a para-toluenesulfonate. Examples of the base addition salt include an inorganic base salt such as a sodium salt, a potassium salt, a calcium salt, a magnesium salt, and an ammonium salt, and an organic base salt such as a triethylammonium salt, a triethanolammonium salt, a pyridinium salt, and diisopropylammonium salt. Further examples thereof include an amino acid salt such as a basic or acidic amino acid, for example, arginine, aspartic acid, and glutamic acid. Examples of the preferred pharmaceutically acceptable salts of the above four compounds include a hydrochloride, a potassium salt, and a sodium salt.

The above four compounds or pharmaceutically acceptable salts thereof may be present as a hydrate or a solvate. In the present invention, the above four compounds in a free form or in a form of a pharmaceutically acceptable salt, as well as a hydrate or solvate thereof can be utilized.

As to the above four compounds or pharmaceutically acceptable salts thereof, those already sold as a medicament or those produced by a known method can also be used.

The above four compounds or pharmaceutically acceptable salts thereof can be used as an active ingredient in a vascular endothelial cell protective agent, a BBSCB protective agent, a blood-organ barrier protective agent, a central nervous system protective agent, and a pharmaceutical composition for preventing and/or treating a disease accompanied with a BBSCB disorder as described later.

As to these agents and composition, "including at least one compound selected from the group consisting of mubritinib, brexpiprazole, papaverine, a bismuth-containing compound, and pharmaceutically acceptable salts thereof" means including at least any one among one compound selected from the group consisting of mubritinib and a pharmaceutically acceptable salt thereof, one compound selected from the group consisting of brexpiprazole and a pharmaceutically acceptable salt, one compound selected from the group consisting of papaverine and a pharmaceutically acceptable salt thereof, and one compound selected from the group consisting of a bismuth-containing compound and a pharmaceutically acceptable salt thereof, and encompasses including two or more compounds among these compounds.

Similarly, "including at least one compound selected from the group consisting of a bismuth-containing compound, papaverine, and pharmaceutically acceptable salts thereof" means including at least any one among one compound selected from the group consisting of papaverine and a pharmaceutically acceptable salt thereof, and one compound selected from the group consisting of a bismuth-containing compound and a pharmaceutically acceptable salt, and encompasses including two or more compounds among these compounds.

In addition, "including at least one compound selected from the group consisting of a bismuth-containing compound and a pharmaceutically acceptable salt thereof" means including at least one compound selected from the group consisting of a bismuth-containing compound and a pharmaceutically acceptable salt, and encompasses including two or more compounds among these compounds.

Vascular Endothelial Cell Protective Agent

The above four compounds and pharmaceutically acceptable salts thereof have an ability to protect vascular endothelial cells, and thus can be used as a vascular endothelial cell protective agent. In the present invention, the vascular endothelial cell protective agent means a substance having an ability to protect vascular endothelial cells from external or internal stress and prevent damage to vascular endothelial cells, for example, cell death or a deterioration in cell function. In the present invention, the vascular endothelial cell protective agent can be used for any vascular endothelial cell, for example, vascular endothelial cells of a peripheral blood vessel or vascular endothelial cells of a blood vessel existing in the central nervous system. In the present invention, the vascular endothelial cell protective agent is particularly suitable for protecting vascular endothelial cells present in the brain or spinal cord.

Thus, one aspect of the present invention provides a vascular endothelial cell protective agent including at least one compound selected from the group consisting of mubritinib, brexpiprazole, papaverine, a bismuth-containing compound, and pharmaceutically acceptable salts thereof. The vascular endothelial cell protective agent preferably includes at least one compound selected from the group consisting of a bismuth-containing compound, papaverine, and pharmaceutically acceptable salts thereof. The vascular endothelial cell protective agent more preferably includes at least one compound selected from the group consisting of a bismuth-containing compound and a pharmaceutically acceptable salt thereof. Descriptions of each compound and pharmaceutically acceptable salt thereof and examples of compounds and salts including those preferably used, are as described above.

BBSCB Protective Agent

The vascular endothelial cell protective agent can protect the BBSCB through protection of CNS vascular endothelial cells, thereby being able to suppress the occurrence and extent of a BBSCB disorder under stress loading such as primary injury in spinal cord injury. Therefore, the vascular endothelial cell protective agent can also be used as a BBSCB protective agent and this BBSCB protective agent is also one aspect of the present invention. In the present invention, the BBSCB protective agent means a substance having an ability to protect the BBSCB from external or internal stress that causes disorder of the BBSCB and prevent a deterioration in its function, particularly the barrier function that restricts the exchange of substances between blood and central nerve tissue fluid based on the selective material permeability of the tight junction. In the present invention, the BBSCB protective agent is particularly suitable for protecting the blood-brain barrier (BBB) or the blood-spinal cord barrier (BSCB).

Thus, one aspect of the present invention provides a BBSCB protective agent including at least one compound selected from the group consisting of mubritinib, brexpiprazole, papaverine, a bismuth-containing compound, and pharmaceutically acceptable salts thereof. The BBSCB protective agent preferably includes at least one compound selected from the group consisting of a bismuth-containing compound, papaverine, and pharmaceutically acceptable salts thereof. The BBSCB protective agent more preferably includes at least one compound selected from the group consisting of a bismuth-containing compound and a pharmaceutically acceptable salt thereof. Descriptions of each compound and pharmaceutically acceptable salt thereof, and examples of compounds and salts including those preferably used, are as described above.

In CNS infarction, typically cerebral infarction, the risk of brain hemorrhage due to BBB disorder is so high that use of a thrombolytic agent such as tissue plasminogen activator (t-PA) is limited to within 4.5 hours after onset. Since the BBSCB protective agent can reduce the risk of brain hemorrhage in patients with cerebral infarction through protective effect for the BBB, it is expected to enable use of a thrombolytic agent in patients with cerebral infarction for which the use of a thrombolytic agent has been conventionally avoided. Thus, the present invention also encompasses use of the BBSCB protective agent in combination with the thrombolytic agent, with the intention of extending the treatable time with the thrombolytic agent.

In addition to the BBSCB, there are other blood-organ barriers in a living body that function as barriers to restrict the exchange of substances between blood and organs. Since vascular endothelial cells also bear a barrier function in the blood-organ barriers as in the BBSCB, the vascular endothelial cell protective agent can also be used as a protective agent for blood organ barriers other than the BBSCB, and this blood-organ barrier protective agent is also one aspect of the present invention. Examples of the blood-organ barrier other than the BBSCB include the blood-retinal barrier, the blood-bile barrier, the blood-thymus barrier, the blood-testis barrier, and the blood-nerve barrier.

Thus, one aspect of the present invention provides a blood-organ barrier protective agent including at least one compound selected from the group consisting of mubritinib, brexpiprazole, papaverine, a bismuth-containing compound, and pharmaceutically acceptable salts thereof. The blood-organ barrier protective agent preferably includes at least one compound selected from the group consisting of a bismuth-containing compound, papaverine, and pharmaceutically acceptable salts thereof. The blood-organ barrier protective agent more preferably includes at least one compound selected from the group consisting of a bismuth-containing compound and a pharmaceutically acceptable salt thereof. Descriptions of each compound and pharmaceutically acceptable salt thereof and examples of each compound and salt including those preferably used, are as described above.

Central Nervous System Protective Agent

The vascular endothelial cell protective agent can suppress damage of the CNS (such as secondary injury in spinal cord injury) accompanied with a BBSCB disorder through suppression of the BBSCB disorder by protecting the BBSCB, and can protect CNS. Therefore, the vascular endothelial cell protective agent can also be used as a CNS protective agent and this CNS protective agent is also one aspect of the present invention. In the present invention, the CNS protective agent means a substance having an ability to protect CNS cells from external or internal stress and prevent damage to cells in CNS accompanied with a BBSCB disorder, for example, cell death or a deterioration in cell function. In the present invention, the CNS protective agent is particularly suitable for protecting the brain or the spinal cord from secondary damage in brain injury, spinal cord injury, or compressive myelopathy.

Thus, one aspect of the present invention provides a CNS protective agent including at least one compound selected from the group consisting of mubritinib, brexpiprazole, papaverine, a bismuth-containing compound, and pharmaceutically acceptable salts thereof. The central nervous system protective agent preferably includes at least one compound selected from the group consisting of a bismuth-containing compound, papaverine, and pharmaceutically acceptable salts thereof. The CNS protective agent more preferably includes at least one compound selected from the group consisting of a bismuth-containing compound and a pharmaceutically acceptable salt thereof. Descriptions of each compound and pharmaceutically acceptable salt thereof and examples of compounds and salts including those preferably used, are as described above.

Pharmaceutical Composition

As described above, mubritinib, brexpiprazole, papaverine, a bismuth-containing compound, and pharmaceutically acceptable salts thereof have the protective effect for the vascular endothelial cells, the BBSCB, and the CNS, and thus can be used for preventing and/or treating a disease accompanied with a BBSCB disorder. Therefore, another aspect of the present invention provides a pharmaceutical composition including at least one compound selected from the group consisting of mubritinib, brexpiprazole, papaverine, a bismuth-containing compound, and pharmaceutically acceptable salts thereof for preventing and/or treating a disease accompanied with a BBSCB disorder. The pharmaceutical composition preferably includes at least one compound selected from the group consisting of a bismuth-containing compound, papaverine, and pharmaceutically acceptable salts thereof. The pharmaceutical composition more preferably includes at least one compound selected from the group consisting of a bismuth-containing compound and a pharmaceutically acceptable salt thereof. Descriptions of each compound and pharmaceutically acceptable salt thereof and examples of compounds and salts including those preferably used, are as described above.

BBSCB disorder means a condition in which the function of the BBSCB is reduced or disrupted as a result of some abnormality in the BBSCB, resulting in increased material permeability. Moreover, the disease accompanied with a BBSCB disorder is a disease in which the permeability of the BBSCB is increased, and includes a disease caused by increased permeability of the BBSCB and a disease exacerbated by increased permeability of the BBSCB. Examples of the disease accompanied with a BBSCB disorder include injury of the CNS such as brain injury and spinal cord injury; infarction of the CNS such as cerebral infarction and spinal cord infarction; hemorrhage of the CNS such as brain hemorrhage and spinal cord hemorrhage; an inflammatory disease of the central nervous system such as multiple sclerosis, encephalomyelitis, and optic neuritis; a degenerative disease of the central nervous system such as Alzheimer's disease, Parkinson's disease, and amyotrophic lateral sclerosis; a symptomatic neurological disease such as dementia and epilepsy; a spinal cord disorder accompanied with spine degeneration such compressive myelopathy, a BBSCB disorder due to a drug such as an immunosuppressant (for example, harmful symptoms such as tremor, delirium, and abnormal behavior); an infection and anaphylaxis of the central nervous system due to the transfer of viruses and allergens(for example, Neuron 2008, 57(2): 178-201; Nat Med. 2013, 19(12): 1584-96, Physiol Rev, 2019 Jan. 1; 99(1): 21-78. doi: 10.1152/physrev.00050.2017). In the present invention, the pharmaceutical composition is particularly suitable for treating brain injury, spinal cord injury, or compressive myelopathy.

As used herein, the term "prevention" encompasses all types of medically acceptable prophylactic interventions aimed at inhibiting or suppressing the affection or onset of a disease. In addition, the term "treatment" encompasses all types of medically acceptable therapeutic interventions aimed at cure or temporary remission of a disease. That is, prevention and/or treatment of a disease accompanied with a BBSCB disorder encompasses a medically acceptable intervention for various purposes including delaying or stopping progression of a disease accompanied with a BBSCB disorder, regression or disappearance of a lesion, prevention of the onset, inhibition of the recurrence, and the like.

The pharmaceutical composition includes at least one compound (active ingredient) selected from the group consisting of mubritinib, brexpiprazole, papaverine, a bismuth-containing compound and pharmaceutically acceptable salts thereof, and a pharmaceutically acceptable ingredient. Examples of the pharmaceutically acceptable ingredient include drugs other than the above active ingredients (for example, a thrombolytic agent and the like), a buffer, an antioxidant, a preservative, protein, a hydrophilic polymer, amino acid, a chelating agent, a nonionic surfactant, an excipient, a stabilizer, and a carrier. The pharmaceutically acceptable ingredient is well known to those skilled in the art, and can be appropriately selected from ingredients described in, for example, the Japanese Pharmacopoeia, 17$^{th}$ edition and other standards, according to the form of the preparation within a range of the normal ability to be carried out by those skilled in the art for use.

The dosage form of the pharmaceutical composition can be any form, and preferred examples thereof include the forms of oral preparations (tablets, capsules, powders, granules, fine granules, pills, suspensions, emulsions, liquids, syrups, and the like) and parenteral preparations (injections, infusions, external preparations, and the like).

The administration route of the pharmaceutical composition is not particularly limited. Examples of the administration for a parenteral preparation include intravascular administration (preferably an intravenous administration), intraperitoneal administration, intestinal administration, and subcutaneous administration. In one of the preferred embodiments, the pharmaceutical composition is administered to a living body by oral administration or intravenous administration.

The pharmaceutical composition is administered in an effective amount for prevention or treatment of a disease accompanied with a BBSCB disorder, which is appropriately determined depending on usage, age of a subject, a state of the disease, and other conditions. The usual dose per 1 kg of body weight for an adult is, in terms of an amount of active ingredient, approximately 10 µg to 200 mg, preferably 20 µg to 100 mg, and more preferably 40 µg to 40 mg for papaverine as the active ingredient; approximately 0.5 µg to 10 mg, preferably 1 µg to 5 mg, and more preferably 2 µg to 2 mg for mubritinib or brexpiprazole as the active ingredient; approximately 250 µg to 5000 mg, preferably 500 µg to 2500 mg, and more preferably 1 mg to 1000 mg for bismuth subnitrate, being an example of a bismuth-containing compound, as the active ingredient. The effective amount of pharmaceutical composition can be administered once or in multiple doses daily, or intermittently.

Another aspect of the present invention also provides a method for preventing and/or treating a disease accompanied with a BBSCB disorder, including administering an effective amount of at least one compound selected from the group consisting of the above four compounds and pharmaceutically acceptable salts to a subject in need thereof.

The present invention will be described in more detail with reference to the following examples, but the present invention is not limited thereto. In the examples, experimental data was expressed as mean±standard error, unless otherwise specified. Statistical analysis was performed using statistical analysis software JMP Pro 11.0 (SAS Institute). Student's t-test was used for comparing between two groups. Tukey's test was used for comparing between multiple groups. A p-value of less than 0.05 was considered significant.

EXAMPLES

Example 1

Evaluation of Protective Effect on Vascular Endothelial Cells (In Vitro)

The protective effect of papaverine, mubritinib, brexpiprazole, and bismuth subnitrate on vascular endothelial cells were evaluated using a monolayer culture model of rat brain endothelial cells (RBECs) after being subjected to oxygen-glucose deprivation/reoxygenation (OGD/R).

Papaverine and mubritinib were purchased from Tokyo Chemical Industry Co., Ltd., brexpiprazole was purchased from Funakoshi Co., Ltd., bismuth subnitrate was purchased from Santa Cruz Biotechnology, Inc. (USA), and they were used as test compounds.

For primary culture of RBECs, brain tissue from 3-week-old rats was shredded to 1 cm$^3$ or less, enzymatically treated with type II collagenase (1 mg/ml, Worthington Biochemical Corp., USA) and DNase (15 µg/ml) at 37° C. for 1.5 hours with shaking. Capillary pieces in the obtained cell pellets were treated with collagenase-dispase (1 mg/ml, Roche Applied Sciences, Switzerland) and DNase (6.7 µg/ml) at 37° C. for 45 minutes. RBEC cell pellets were separated with 33% Percoll (Pharmacia, Sweden), the capillary piece-containing layer was collected and seeded in a 35 mm plastic dish coated with type IV collagen (0.1 mg/ml) and fibronectin (0.1 mg/ml) (Day 0). RBECs were cultured in RBEC I medium (DMEM/F12, 10% fetal bovine plasma derived from serum (PDS) (Animal Technologies, Inc., USA), basic fibroblast growth factor (bFGF, Roche Applied Sciences, 1.5 ng/ml), heparin (100 μg/ml), insulin (5 μg/ml), transferrin (5 μg/ml), sodium selenite (5 ng/ml) (insulin-transferrin-sodium selenite media supplement), gentamycin (50 μg/ml), puromycin (4 μg/ml)). After Day 3, the medium was replaced with RBEC I medium excluding puromycin (RBEC II medium). At the stage where the cultured cells reached 80% confluent, the purified endothelial cells were treated with trypsin (0.05% w/v)-EDTA (0.02% w/v) solution for a short time and passaged (Day 4).

The above prepared RBECs were seeded to $2.0 \times 10^5$ cell/cm$^2$ on the polyester membrane on the upper side of the Transwell insert for a 24-well plate coated with collagen and fibronectin, and cultured in DMEM/F12 containing 4.5 g/L (concentration) of glucose under normoxic condition (20% oxygen) or in DMEM/F12 containing no glucose under anoxic condition at 37° C. for 6 hours. The medium was replaced with RBEC medium added with the test compound, and then cultured for another 18 hours under normoxic condition. Other wells in which the medium added with the test compound was replaced with a medium added with DMSO at the same concentration (0.1%) were prepared and used as controls.

The permeability of Na—F, which is an index of paracellular transport through the tight junction (TJ), was evaluated in a monolayer culture model of RBECs. The above-described Transwell insert in which the cells were cultured was transferred to a 24-well plate, and 0.9 mL of Dulbecco's PBS (assay buffer (pH 7.4)) containing 4.5 g/L glucose and 10 mM Hepes was added thereto. 0.5 ml of buffer containing 10 μg/ml Na—F (molecular weight: 376 Da) was added to the insert instead of the medium. After 15 and 45 minutes from the addition of Na—F, the insert was transferred to another well containing the assay buffer and measurement was carried out at 535 nm (excitation wavelength: 485 nm) using Wallac 1420 ARVO Multilabel Counter (Perkin Elmer, Waltham, MA, USA). The permeability of Na—F is expressed by the effective permeability coefficient Pe (cm/s) and calculated based on Fick's law.

The results are illustrated in FIG. 1. All of the test compounds significantly reduced the permeability of Na—F, which was enhanced due to being subjected to OGD/R, indicating that they had a protective effect on RBECs from the stress caused by OGD/R.

Example 2

Evaluation of Protective Effect on BBSCB (In Vitro)

The protective effect of papaverine, mubritinib, brexpiprazole, and bismuth subnitrate on the BBSCB was evaluated by being subjected to OGD/R in an in vitro BBSCB co-culture model using RBECs, rat brain-derived astrocytes, and rat brain-derived pericytes.

Rat brain-derived astrocytes were prepared as follows. Brain cortex pieces of newborn rats were mechanically isolated in astrocyte culture medium (10% fetal bovine serum-containing DMEM) and seeded in culture flasks. In order to obtain type 1 astrocytes, the culture flasks after becoming confluent were shaken at 37° C. overnight, and floating cells were collected and cultured. The purity of astrocytes was confirmed by immunostaining for glial fibrous acidic protein (GFAP), and astrocytes were cryopreserved in CELLBANKER (Zenoaq, Koriyama, Japan). Cells from the second passage were used.

Rat brain-derived pericytes were prepared as follows. RBECs were prepared in the same manner as in Example 1 and seeded in uncoated plastic dishes with DMEM containing 10% FBS. The medium was replaced every 3 days for 2 weeks and pericytes were cryopreserved in CELLBANKER.

Next, an in vitro BBSCB co-culture model was prepared as follows. Transwell insert for a 24-well plate turned upside down, and pericytes ($2.0 \times 10^4$ cell/cm$^2$) were placed in a hemispherical shape on the polycarbonate membrane coated with collagen on the lower side of the insert and cultured for 3 hours to adhere. Astrocytes were seeded on the bottom of the plate ($1.0 \times 10^5$ cell/cm$^2$). After adhesion overnight, RBECs prepared in the same manner as in Example 1 were seeded on the polyester membrane on the upper side of the Transwell insert coated with collagen and fibronectin ($2.0 \times 10^5$ cell/cm$^2$) (day 4). In the BBSCB co-culture model, RBEC II medium containing 500 nM hydrocortisone was used.

Figure 2:
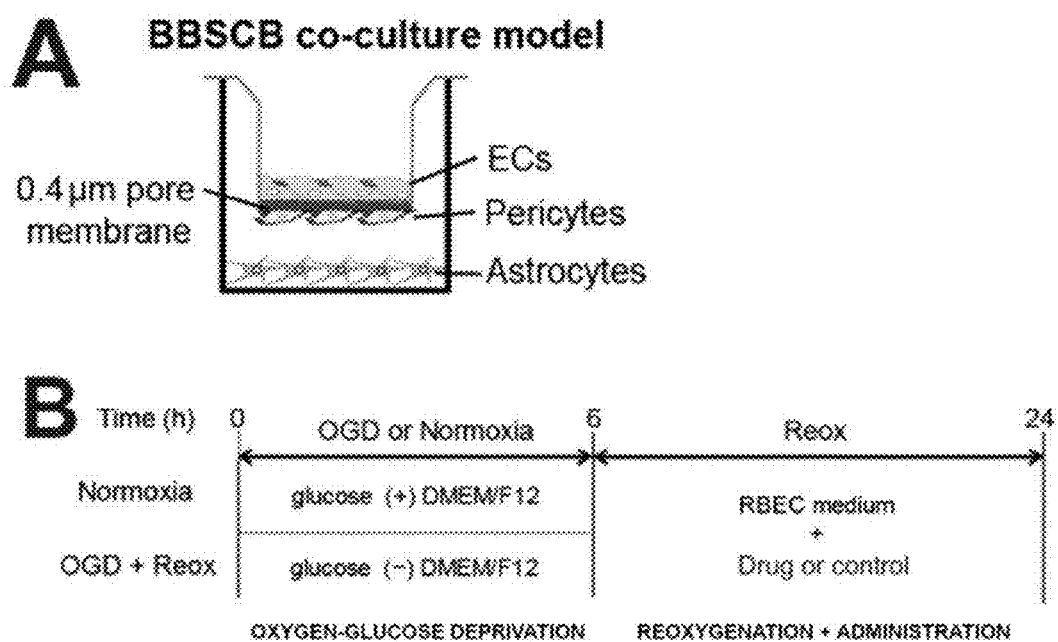
FIG. 2A is a diagram of an outline of a BBSCB model.
FIG. 2B is a diagram of a schedule of an oxygen-glucose deprivation/reoxygenation test.

Next, the cells were cultured in DMEM/F12 containing 4.5 g/L (concentration) of glucose under normoxic condition (20% oxygen) or in DMEM/F12 containing no glucose under anoxic condition, at 37° C. for 6 hours. After the medium was replaced with RBEC medium added with the test compound, the cells were cultured for another 18 hours under normoxic condition (FIG. 2B). Other wells in which the medium was replaced with a medium added with DMSO at the same concentration (0.1%) instead of the medium with the test compound were prepared and used as controls.

Figure 3:
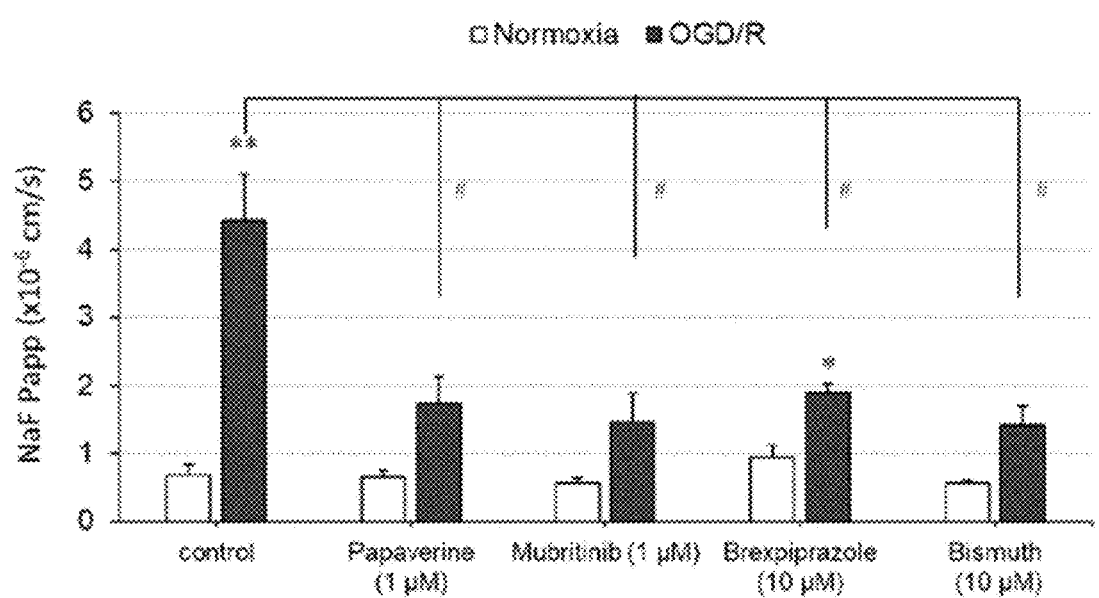
FIG. 3 is a graph of the permeability of Na—F of the BBSCB model in the presence of papaverine, mubritinib, brexpiprazole, or bismuth subnitrate.

The permeability of Na—F, which is an index of paracellular transport through the tight junction (TJ), was evaluated in the same manner as in Example 1. The results are illustrated in FIG. 3. All of the test compounds significantly reduced the permeability of Na—F, which was enhanced by being subjected to OGD/R. Therefore, it was indicated that these compounds had a protective effect on the BBSCB tight junction function.

Example 3

Evaluation of Protective Effect on BBSCB (In Vivo, Spinal Cord Partially Transected Model)

C57BL/6 mice (male, 8 to 13 weeks old, n=5/group) were intraperitoneally administered 200 μL of the test compound dissolved in saline or DMSO, or vehicle. The doses were 20 mg/kg body weight of papaverine, 1 mg/kg body weight of mubritinib, 1 mg/kg body weight of brexpiprazole, and 500 mg/kg body weight of bismuth subnitrate. On the next day after administration, the mice were immobilized in a stereotaxic frame under anesthesia, the posterior cord of the spinal cord was partially transected at the high level of the fourth cervical cord (C4) of the mice using a wire knife, and the same amount of the test compound was intraperitoneally administered again. On the next day after partially transecting the spinal cord, the mice were perfused with PBS to remove blood, followed by the perfusion of PBS with 4% paraformaldehyde for fixing After perfusion, the 3 mm long spinal cord centering the injury site was dissected.

Sagittal sections of the dissected spinal cords at a 30 μm thickness were prepared using a microtome (REM-710, Yamato, Japan), and every 6 sections were used for each staining. Blocking was performed for 1 hour in Tris buffer saline (TBS; pH 8.4) containing 5% Normal horse serum (Thermo Fisher Scientific, Waltham, MA) and 0.25% Triton X-100 (Sigma-Aldrich, St. Louis, MO), and then staining was performed overnight at 4° C. in TBS containing an antibody (Alexa 488 conjugated donkey secondary antibody (1:1000, Jackson immunoresearch, West 14 Grove, PA)). The sections were placed on microscope slides (Platinum Pro, Matsunami Glass Ind., Japan) and dried, covered with Mowiol (Sigma-Aldrich, MO, USA), and then covered with cover glasses (NEO cover glass, Matsunami Glass Ind., Japan) for observation. For tissue evaluation, a single sagittal section of the center of the injured part was used, and was observed using a fluorescence microscope (Keyence BX-710, Osaka, Japan) (100 magnifications). For evaluation of the IgG-stained area, taken images were binarized into black and white using Photoshop CS3 (Adobe, CA, USA), and then quantified using Image J (Schneider et al., 2012). The position 5 mm rostral from the injury was standardized as normal tissue. All quantitative evaluations were performed with the slides blinded.

Figure 4:
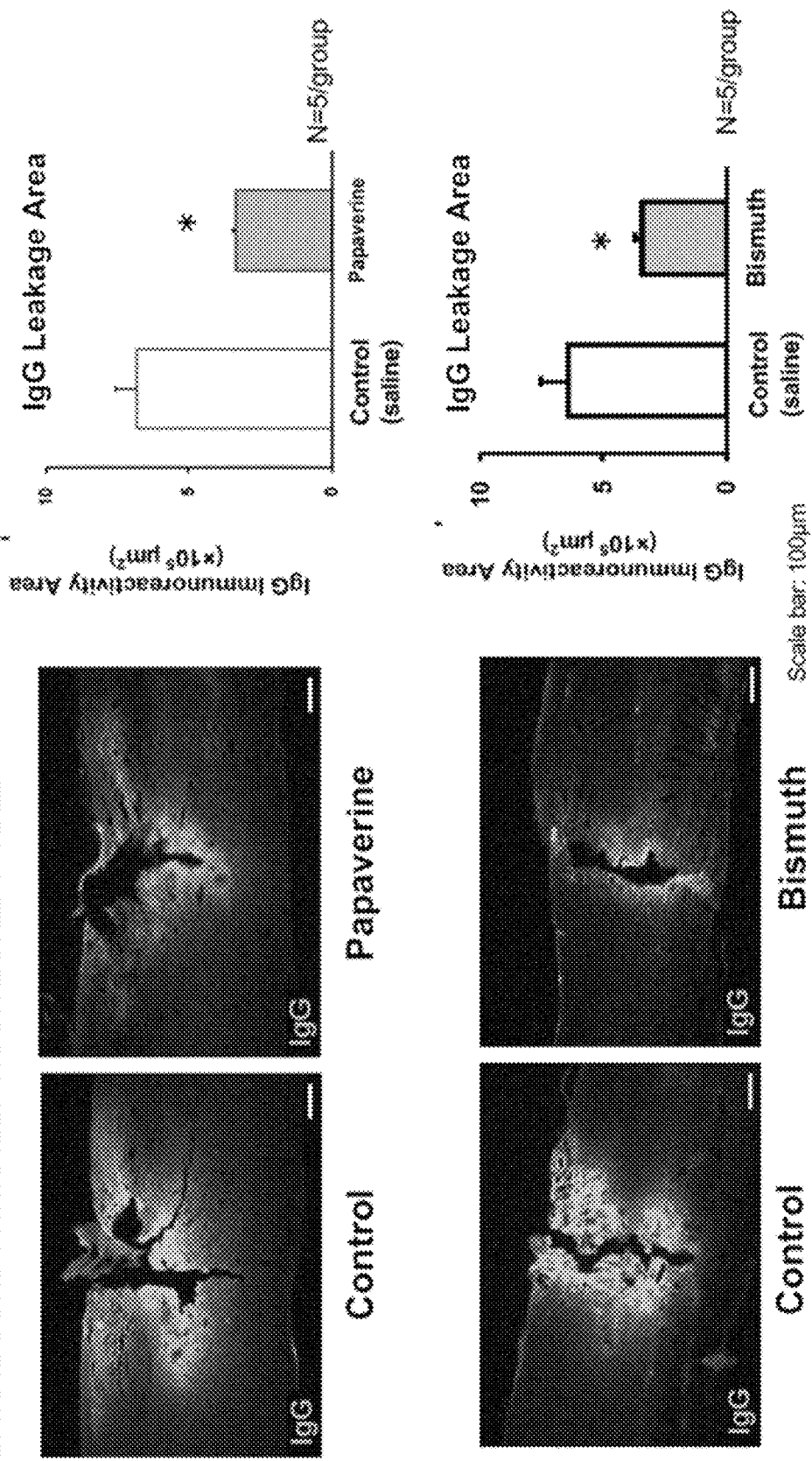
FIG. 4 includes representative photographs of spinal cord tissue sections immunostained with IgG antibody from spinal cord partially transected mice to which papaverine or bismuth subnitrate was administered (The photographs in the center in the figure. The photographs on the left side depict sections of individuals to which saline was administered as a vehicle.) and graphs of the area of IgG positive regions (on the right side in the figure).
Figure 5:
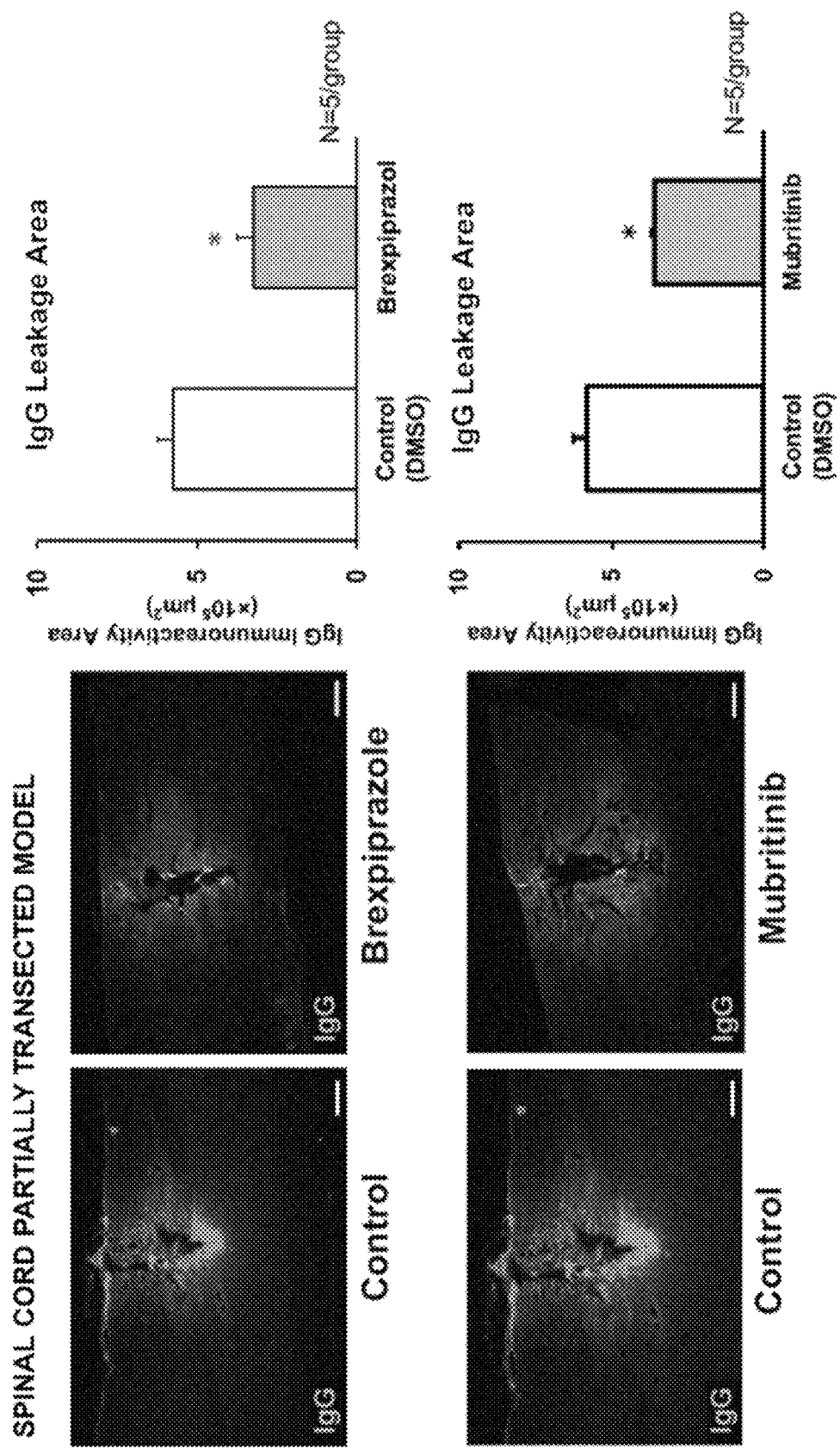
FIG. 5 includes representative photographs of spinal cord tissue sections immunostained with IgG antibody from spinal cord partially transected mice to which mubritinib or brexpiprazole was administered (The photographs in the center in the figure. The photographs on the left side depict sections of individuals to which DMSO was administered as a vehicle.) and graphs of the area of IgG positive regions (on the right side in the figure).

The results are illustrated in FIGS. 4 and 5. In the figures, the torn part from the upper center part to the lower side of each photograph corresponds to the partial transected site of the spinal cord, and the region stained with the anti-IgG antibody around the site corresponds to the IgG leakage region. All of tested four compounds significantly suppressed IgG leakage. Therefore, it was indicated that these compounds had a protective effect on the BBSCB function.

Example 4

Evaluation of Protective Effect on BBSCB (In Vivo, Spinal Cord Crush Injury Model)

Crush injuries were created in the fifth cervical cord (C5) of Lewis rats (female, 8 to 14 weeks old, n=14 to 18/group) under anesthesia by applying a pressure of 200 kdyn using an IH impactor. For seven consecutive days from the day of injury creation, 380 to 420 µL of the test compound dissolved in saline or DMSO, or vehicle was intraperitoneally administered. The daily doses were 20 mg/kg body weight of papaverine, 1 mg/kg body weight of mubritinib, and 1 mg/kg body weight of brexpiprazole. After the rats were kept for 8 weeks from injury creation, histological evaluation and sensory function evaluation for pathological conditions at the chronic stage of the spinal cord injury were performed.

Histological Evaluation

After perfusion and fixation of the rats in the same manner as in Example 3, the 2 cm long spinal cord centering the injury site was dissected. The dissected spinal cords were immersed in PBS containing 30% sucrose for overnight and then transected horizontally to prepare frozen sections having a thickness of 30 µm. After washing the sections with TBS, blocking was performed in a blocking buffer (TBS containing 5% normal horse serum and 0.25% Triton X-100) for 1 hour at room temperature. After washing with PBS, the sections were reacted with a primary antibody at 4° C. overnight. As the primary antibody, purified anti-Glial Fibrillary Acidic Protein (GFAP) Antibody (Biolegend) and Anti-NeuN Antibody, clone A60 (Millipore) were diluted with TBS containing 5% normal horse serum and 0.25% Triton X-100 at 1:1000 and at 1:500, respectively, and used. After washing with TBS, the sections were reacted with a secondary antibody at room temperature for 3 hours. As the secondary antibody, both Alexa Fluor 594 donkey anti-mouse IgG (Jackson ImmunoResearch) and Alexa Fluor 594 donkey anti-chicken IgG (Jackson ImmunoResearch) were diluted with TBS containing 3% normal horse serum and 0.25% Triton X-100 at 1:500, and used. After washing with TBS, the sections were observed using BZ-X710 (KEYENCE) to obtain fluorescent images. For the section of the central part of the spinal cord of the rat, the cavity area of the injured part, the area of the region immunostained with the GFAP antibody, and the number of cells immunostained with the NeuN antibody present on the lines 1.5 mm rostal and caudal from the center of the injury were measured. GFAP is a marker for reactive astrocytes and NeuN is a marker for neurons.

Figure 6:
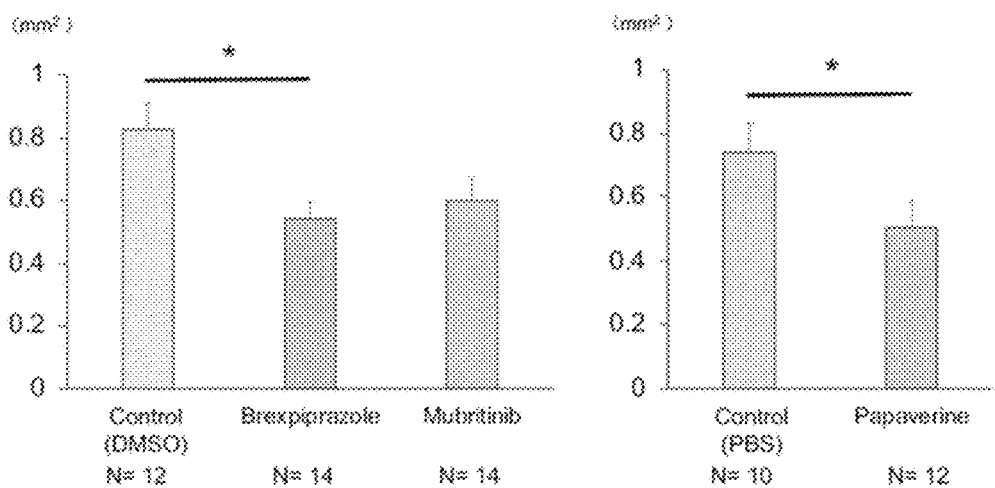
FIG. 6 includes graphs of the area of GFAP positive regions in spinal cord tissue sections of spinal cord crush injury rats to which papaverine, mubritinib, or brexpiprazole was administered.

The GFAP positive area, that is, the reactive astrocyte area is illustrated in FIG. 6. The reactive astrocyte is an index of the glial scars, indicating that the smaller the area of the reactive astrocytes, the smaller the injured range of the spinal cord. The average value of the reactive astrocyte area in all the groups to which the test compound was administered was smaller than that in the vehicle-administrated group, and in particular, papaverine and brexpiprazole significantly reduced the reactive astrocyte area.

Figure 7:
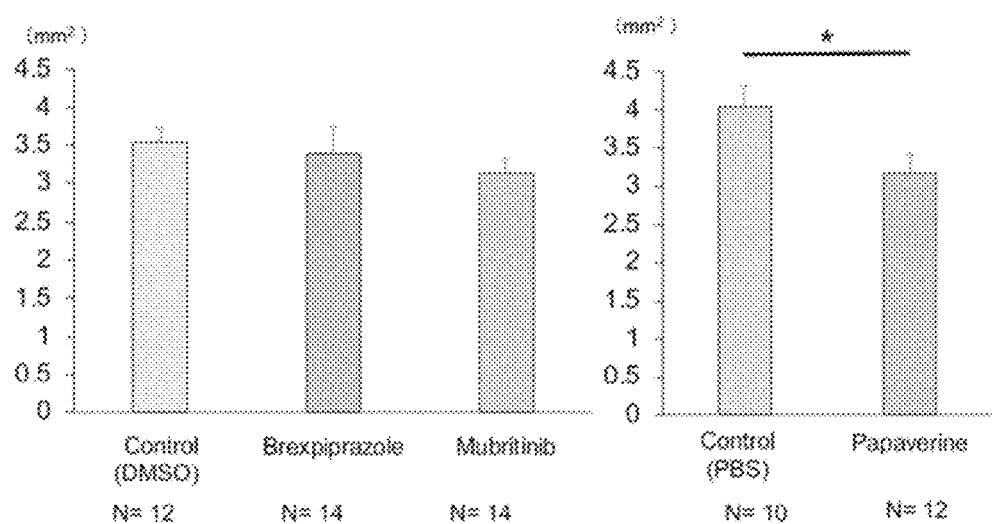
FIG. 7 includes graphs of the cavity area of the injured part in spinal cord tissue sections of spinal cord crush injury rats to which papaverine, mubritinib, or brexpiprazole was administered.

The cavity area of the injured part is illustrated in FIG. 7. The cavity area of the injured part is an index of the degree of spinal cord injury, and when the spinal cord is injured more, the cavity area becomes larger. The average value of the cavity area of the injured part in all the groups to which the test compound was administered was smaller than that in the vehicle-administered group, and in particular, papaverine significantly reduced the cavity area of the injured part.

Figure 8:
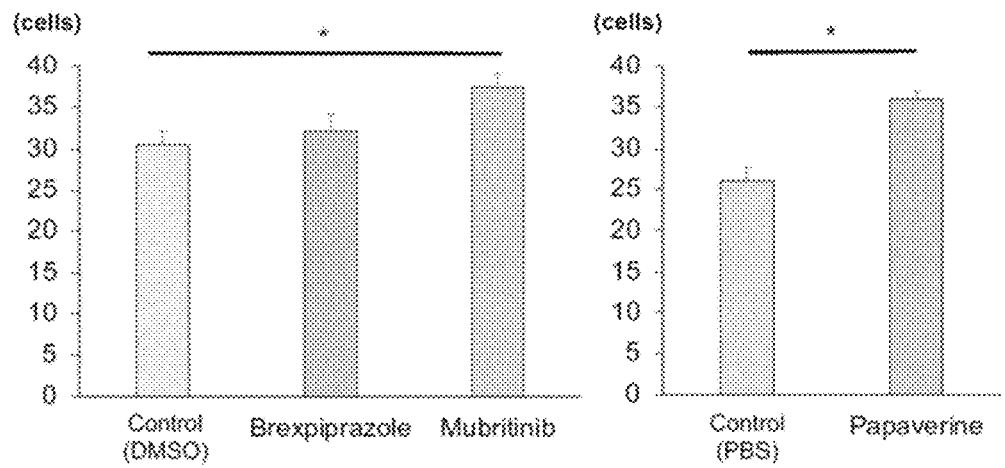
FIG. 8 includes graphs of the number of NeuN-positive cells in spinal cord tissue sections of spinal cord crush injury rats to which papaverine, mubritinib, or brexpiprazole was administered.

The number of NeuN-positive cells, that is, the number of remaining neurons is illustrated in FIG. 8. The average number of remaining neurons in all the groups to which the test compound was administered was larger than that in the vehicle-administered group, and in particular, papaverine and mubritinib significantly increased the number of remaining neurons.

Sensory Function Evaluation

From 1 week before spinal cord injury creation, rats were placed in a dark room for 10 minutes a day for acclimatization. Before and 8 weeks after spinal cord injury creation, the rats were placed in a dark room for 5 minutes, and then subjected to pain stimulation of each limb using Dynamic Plantar Aesthesiometer (UGO BASILE). The stimulus was applied using a 0.5 φ filament (metal) at an increase rate of 2 g/sec, and the time until the rat felt pain and escaped from the filament was measured 3 times for each limb. The interval of each pain stimulus was 3 minutes or longer, and the same limb was not stimulated consecutively.

Figure 9:
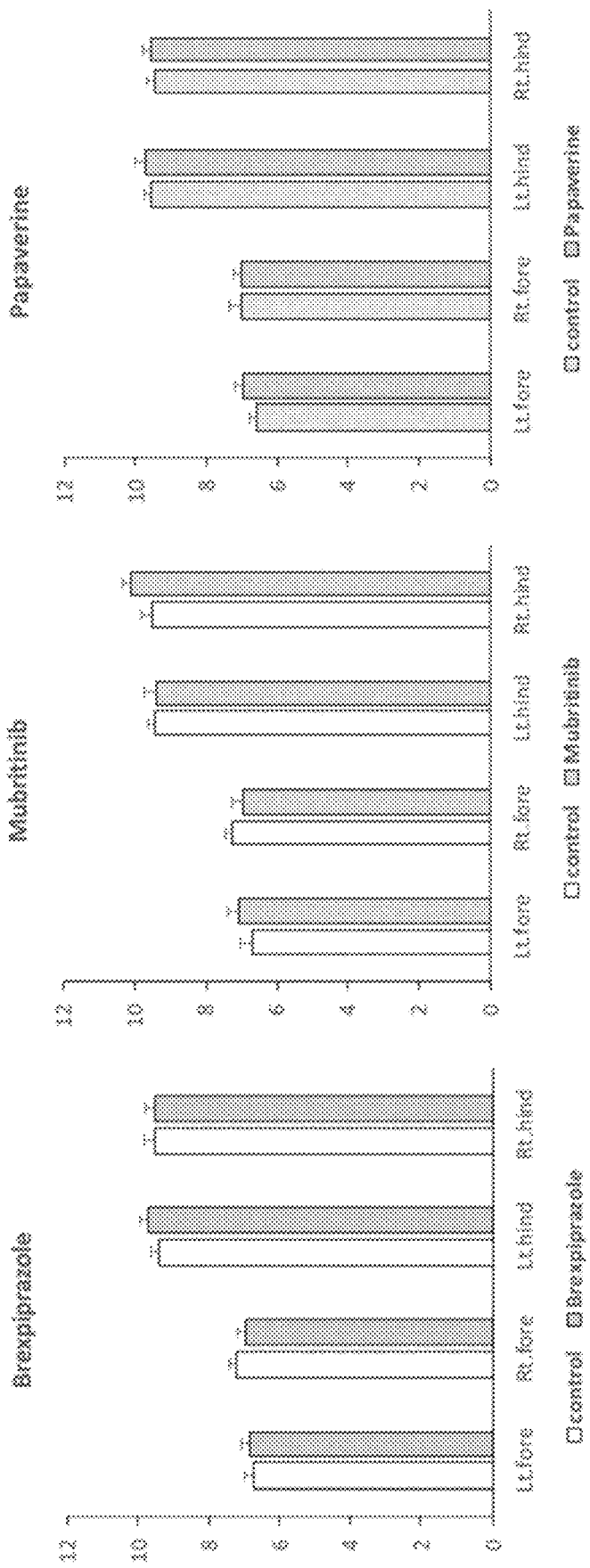
FIG. 9 includes graphs of the stimulus response time of spinal cord crush injury rats to which papaverine, mubritinib or brexpiprazole was administered, measured before spinal cord injury.
Figure 10:
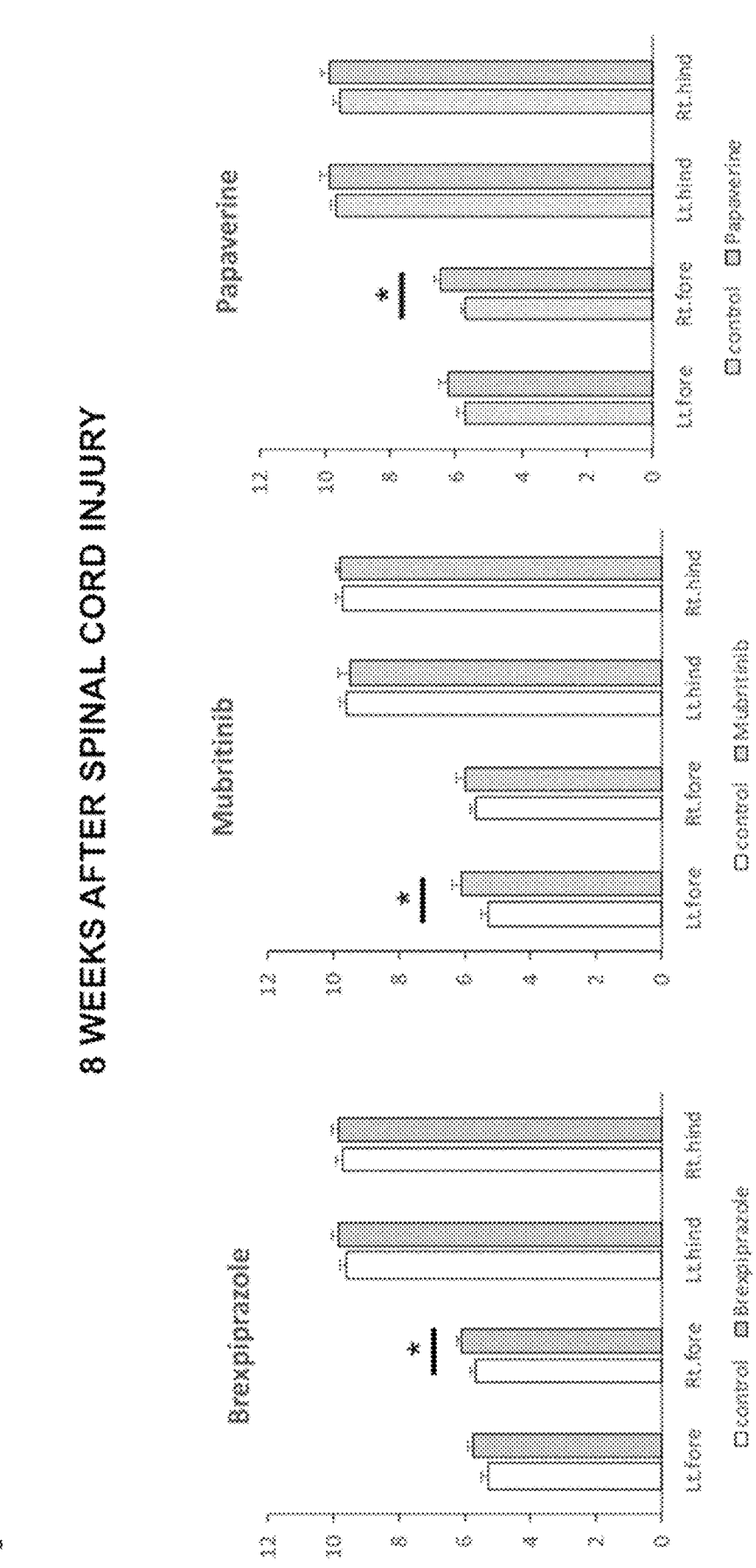
FIG. 10 includes graphs of the stimulus response time of spinal cord crush injury rats to which papaverine, mubritinib, or brexpiprazole was administered, measured after 8 weeks from spinal cord injury.

The time required to respond to the stimulus for each limb is illustrated in FIGS. 9 and 10. It is indicated that the shorter this time, the more sensitive the response to the stimulus. Before injury creation, there was no difference in sensory function between the vehicle-administered group and the test compound-administered group (FIG. 9). After 8 weeks from injury creation, the response time of the upper limbs was shortened in the vehicle-administered group, and a hypersensitive response to the stimulus was observed, whereas the response time of the upper limbs in all the test compound-administered groups was significantly longer than that in the vehicle-administered group, and an improvement in upper limb sensory function was observed (FIG. 10).

From the above results, it was indicated that all the test compounds suppressed an increase in reactive astrocytes, a tissue defect, and loss of neuronal cell bodies, which were the pathological conditions at the chronic stage of the spinal cord injury, and also suppressed a deterioration in sensory function.

Example 5

Evaluation of Protective Effect of Bismuth-Containing Compound on BBSCB (In Vivo, Spinal Cord Crush Injury Model)

Immediately after creating crush injuries in the fifth cervical cord (C5) of Lewis rats (female, 8 to 14 weeks old, n=8/group) under anesthesia in the same manner as in Example 4, 500 mg/kg of bismuth subnitrate dissolved in saline, or vehicle (saline) was intraperitoneally administered. After the rats were kept for 8 weeks from injury creation, histological evaluation and sensory function evaluation were performed for pathological conditions at the chronic stage of the spinal cord injury.

Histological Evaluation

Figure 11:
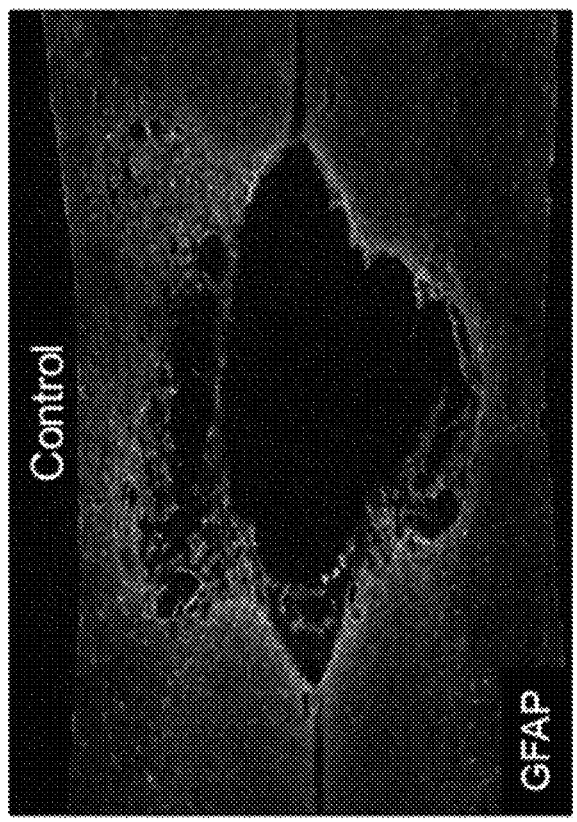
FIG. 11 includes representative photographs of spinal cord tissue sections immunostained with GFAP antibody from spinal cord crush injury model animals to which a single dose of bismuth subnitrate was administered (The photograph on the left side in the upper part of the figure. The photograph on the right side depicts a section of an individual to which saline was administered as a vehicle.), and a graph of the area of GFAP positive regions (lower left in the figure) and a graph of the cavity area of the injured part (lower right in the figure).
Figure 11:
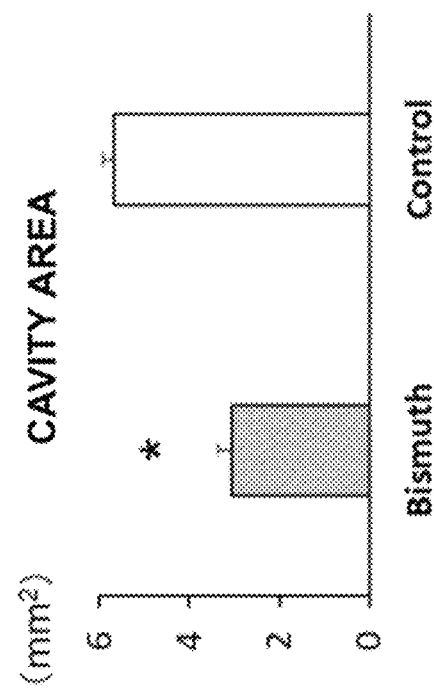
Figure 11:
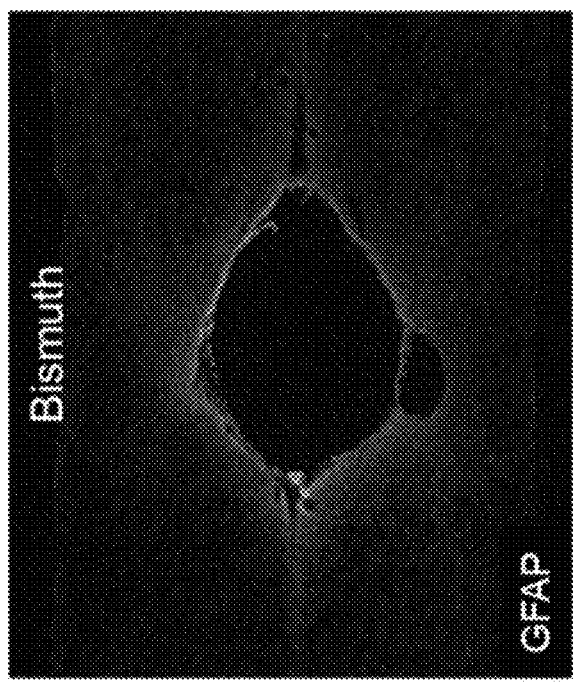
Figure 11:
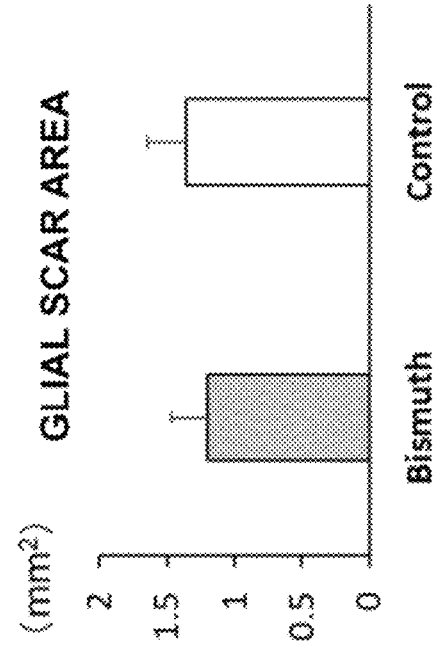
Figure 12:
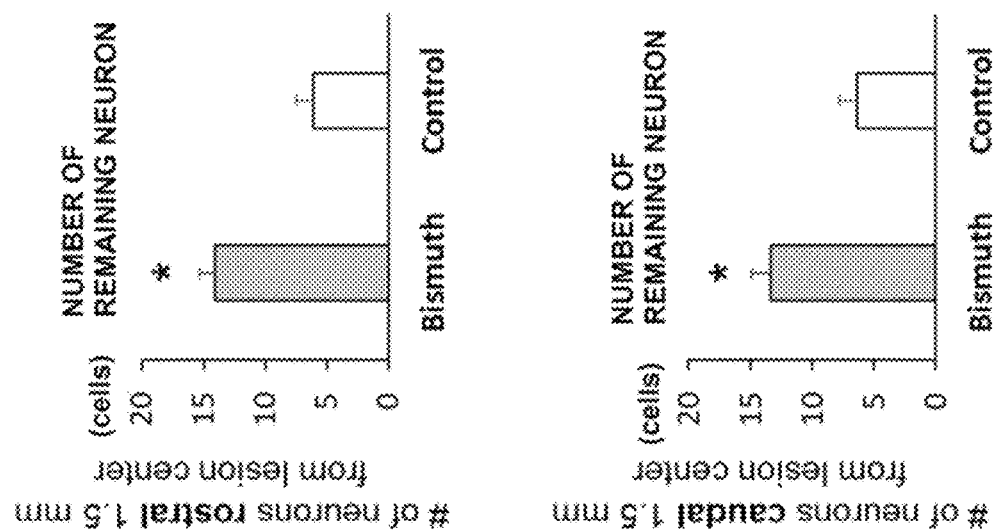
FIG. 12 includes representative photographs of spinal cord tissue sections immunostained with NeuN antibody from spinal cord crush injury model animals to which a single dose of bismuth subnitrate was administered (In the upper part in the figure, a weakly magnified image on the left side and a strongly magnified image in the center. Sections of individuals to which saline was administered as a vehicle on the left side and in the center of the lower part in the figure.), and graphs of the number of NeuN-positive cells present on the line 1.5 mm rostral from the center of the injury (upper right in the figure) and the number of NeuN-positive cells present on the line 1.5 mm caudal to the center of the injury (lower right in the figure).
Figure 12:
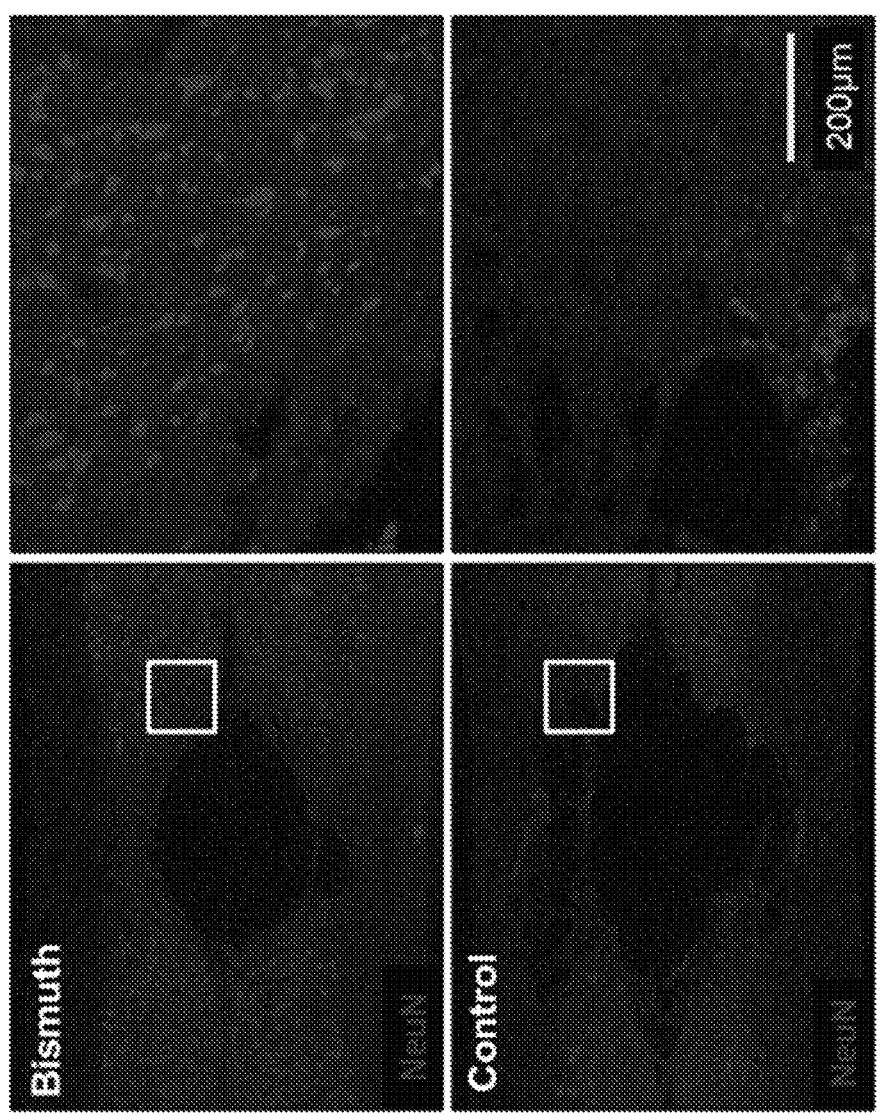

In the same manner as in Example 4, for the section of the central part of the spinal cord of the rat, the reactive astrocyte area, the cavity area of the injured part, and the number of remaining neurons present on the lines 1.5 mm rostal and caudal from the center of the injury were measured. Representative GFAP-immunostained photographs, the reactive astrocyte area, and the cavity area of the injured part are illustrated in FIG. 11. Representative NeuN-immunostained photographs and the number of remaining neurons are illustrated in FIG. 12. In the bismuth subnitrate-administered group, the cavity area of the injured part was significantly reduced compared with that of the vehicle-administered group, and the number of remaining neurons increased both on the rostral side and the caudal side of the injured part.

Sensory Function Evaluation

Figure 13:
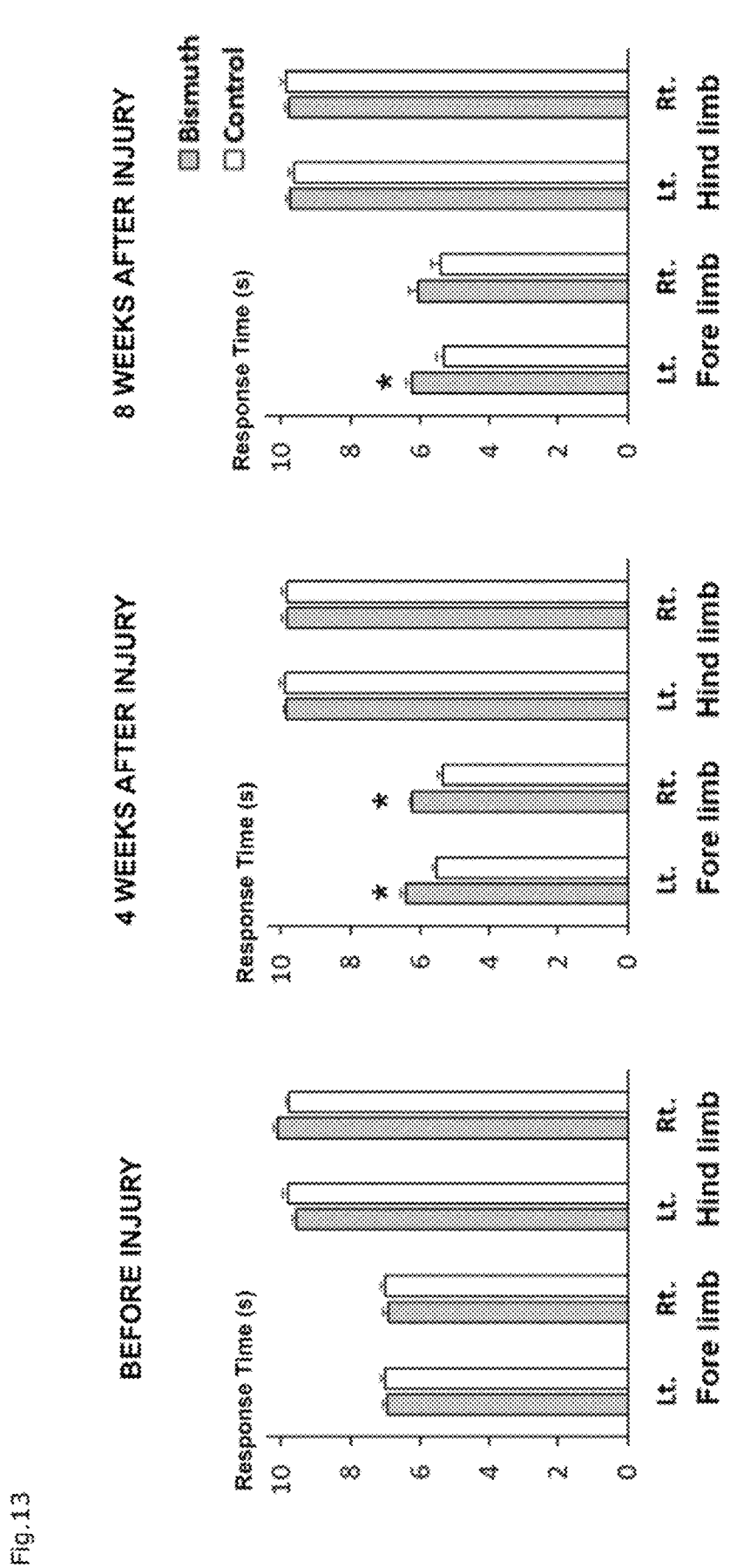
FIG. 13 includes graphs of the stimulus response time of spinal cord crush injury rats to which a single dose of bismuth subnitrate was administered, measured before spinal cord injury, and after 4 weeks and 8 weeks from spinal cord injury.

In the same manner as in Example 4, sensory function evaluation for pain stimulus was performed on rats before, 4 weeks after, and 8 weeks after spinal cord injury creation. The time required to respond to the stimulus for each limb is illustrated in FIG. 13. The response time of the forelimbs in the bismuth subnitrate-administered group was significantly longer than that in the vehicle-administered group, confirming that the sensory function disorder was suppressed.

Walking Function Analysis

Figure 14:
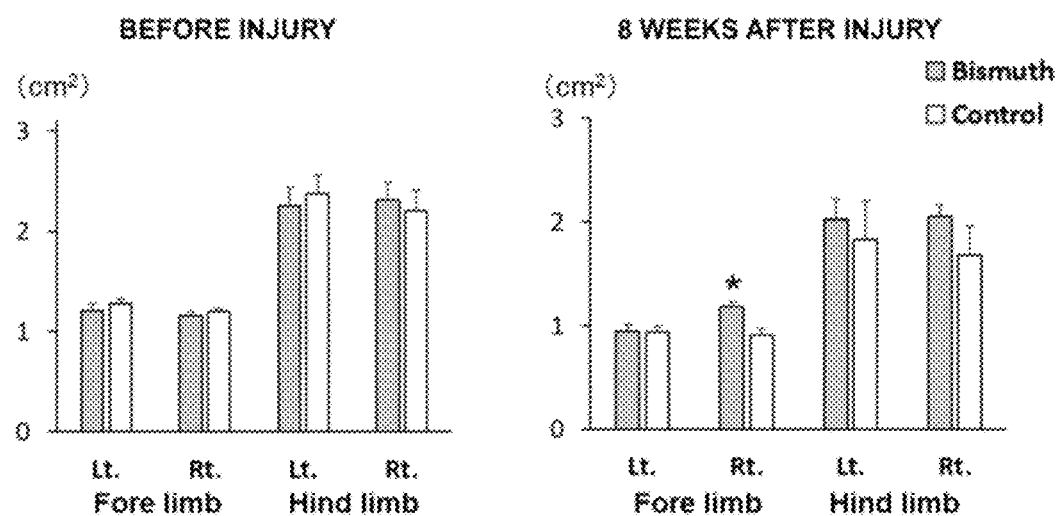
FIG. 14 includes graphs of the ground contacting area (the Paw Area) of each limb of spinal cord crush injury rats to which a single dose of bismuth subnitrate was administered, measured before spinal cord injury and after 8 weeks from spinal cord injury.
Figure 15:
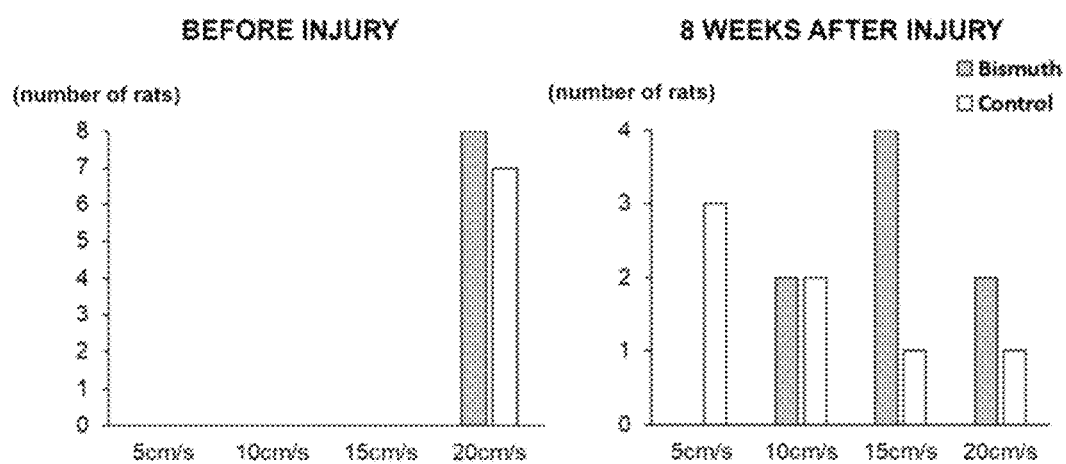
FIG. 15 includes graphs of the maximum walking speed of spinal cord crush injury rats to which a single dose of bismuth subnitrate was administered. The horizontal axis indicates the speed of the treadmill, and the vertical axis indicates the number of rats corresponding to each maximum possible walking speed.

The ground contacting area (the Paw Area) of each leg and the maximum possible walking speed were measured in rats before and 8 weeks after spinal cord injury creation using the DigiGait walking analysis system for small animals (Bioresearch Center Co., Ltd.) according to the manual. In the bismuth subnitrate-administered group, the Paw Area on one side was significantly increased compared with that of the vehicle-administered group (FIG. 14). All rats before spinal cord injury creation were able to walk at a treadmill speed of 20 cm/sec. In the vehicle-administered group, the number of rats that were able to walk at a speed of 15 cm/sec or faster decreased to two individuals, whereas in the bismuth subnitrate-administered group, 6 individuals were able to walk at a speed of 15 cm/sec or faster (FIG. 15).

From the above results, it was indicated that bismuth subnitrate suppressed a tissue defect and loss of neuronal cell bodies, which were the pathological conditions at the chronic stage of the spinal cord injury and also suppressed a deterioration in sensory function and walking function.

Example 6

Evaluation of Protective Effect on BBSCB (In Vivo, Cerebral Cortex Injury Model)

Protection of the BBSCB function in traumatic brain injury by papaverine, mubritinib, brexpiprazole, and bismuth subnitrate was evaluated by observing suppression of IgG leakage from the injured site using the following method.

C57BL/6 mice (male, 8 to 13 weeks old, n=3 to 4/group) were intraperitoneally administered 200 µL of the test compound dissolved in saline or DMSO, or vehicle. The doses were 20 mg/kg body weight of papaverine, 1 mg/kg body weight of mubritinib, 1 mg/kg body weight of brexpiprazole, and 500 mg/kg body weight of bismuth subnitrate. On the next day after administration, injuries were created in the left cerebral hemisphere cortex of the mice under anesthesia by a wire-knife transection method. The mice were immobilized in a stereotaxic frame, and the left lateral 1 mm portion from the bregma of the cranial bone was opened with a microdrill. A wire-knife was inserted into the lateral 1.0 mm from the bregma and 0.5 mm deep in the left cerebral hemisphere, and the wire was extended caudally and pulled up to create the injury. In order to confirm that the injury was completely transverse, no brain tissue remained on the pulled up wire-knife was confirmed. After cerebral cortex injury creation, the same amount of the test compound was intraperitoneally administered again on the same day. On the next day after cerebral cortex injury creation, the mice were perfused with PBS to release blood, followed by fixation with PBS added with 4% paraformaldehyde.

Coronal sections of the excised cerebrum at the 30 µm thickness were prepared using a microtome (REM-710, Yamato, Japan), and every 6 sections were used for each staining. Blocking was performed for 1 hour in Tris buffer saline (TBS; pH 8.4) containing 5% Normal horse serum (Thermo Fisher Scientific, Waltham, MA) and 0.25% Triton X-100 (Sigma-Aldrich, St. Louis, MO), and the sections were then left in TBS containing an anti-IgG antibody Alexa 488 conjugated donkey secondary antibody (1:1000, Jackson immunoresearch, West 14 Grove, PA)) at 4° C. overnight. The sections were placed on microscope slides (Platinum Pro, Matsunami Glass Ind., Japan) and dried, covered with Mowiol (Sigma-Aldrich, MO, USA), and then covered with cover glasses (NEO cover glass, Matsunami Glass Ind., Japan) for observation.

For evaluation of the IgG-stained area, taken images were binarized into black and white using Photoshop CS3 (Adobe, CA, USA), and then quantified using Image J (Schneider et al., 2012). The position 5 mm rostral from the injury was standardized as normal tissue. All quantitative evaluations were performed with the slides blinded. The IgG leakage area was corrected by the depth of injury.

Figure 16:
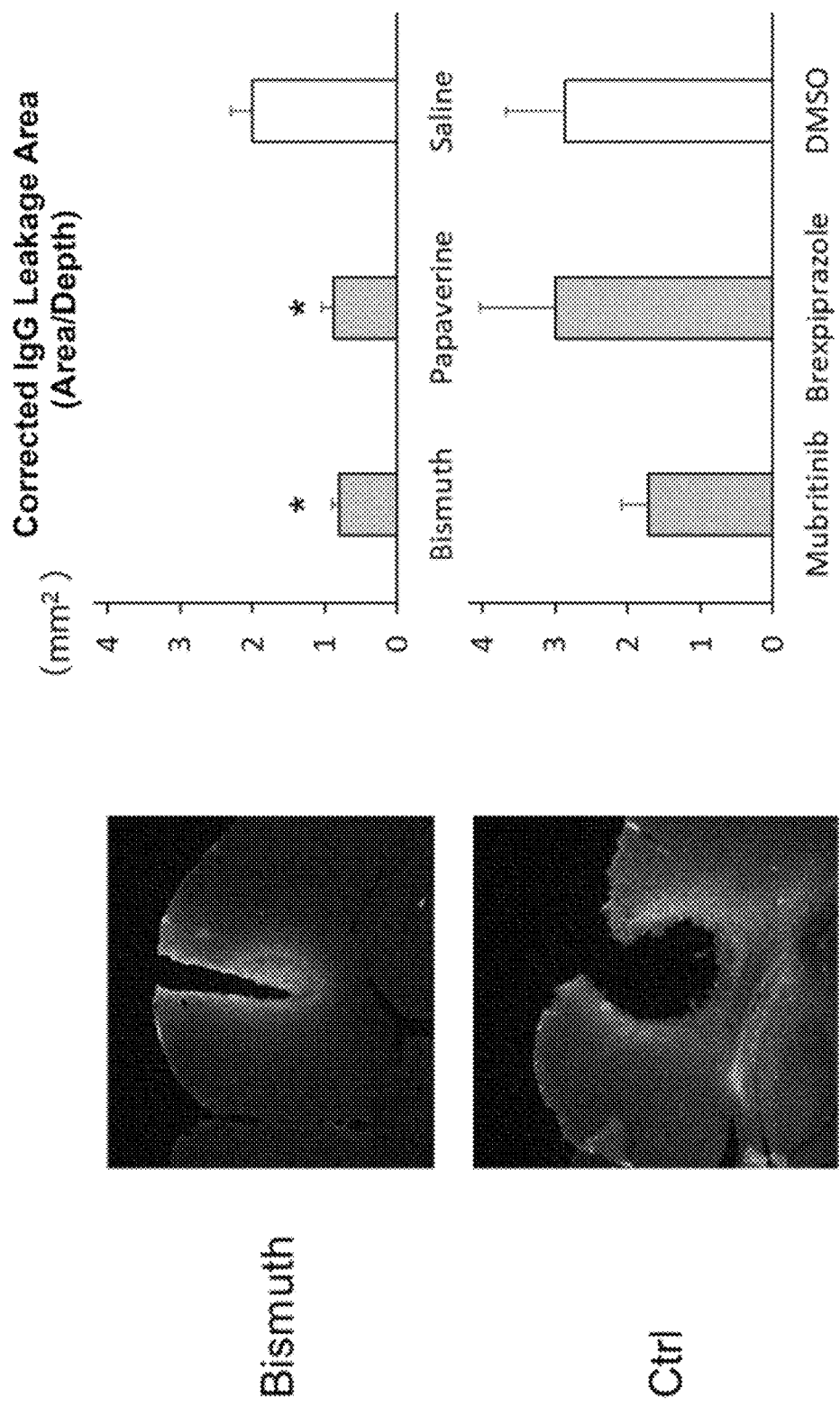
FIG. 16 includes representative photographs of cerebrum tissue sections immunostained with anti-IgG antibody from cerebral cortex injury mice to which papaverine, mubritinib, brexpiprazole, or bismuth subnitrate was administered (In the figure, the photograph of the upper left depicts a section of an individual to which bismuth subnitrate was administered. The photograph of the lower left depicts a section of an individual to which saline or DMSO was administered as a vehicle.), and graphs of the area of IgG positive regions (on the right side in the figure).

A representative photograph of a cerebral cortex tissue section immunostained with anti-IgG antibody of the cerebral cortex injury model mouse to which bismuth subnitrate was administered is shown on the left side of FIG. 16, and respective IgG leakage regions of the mice in bismuth subnitrate, papaverine, mubritinib, and brexpiprazole groups are shown on the right side of FIG. 16. Bismuth subnitrate and papaverine significantly suppressed the leakage of IgG from the injured site of the cerebral cortex. From this result, it was indicated that these compounds had a protective effect on the BBSCB function.

Example 7

Protective Effect on Brain Vascular Endothelial Cells

Human brain vascular endothelial cells (hCMEC/D3, Sigma) were seeded to 5,000 cells/cm$^2$ on a 96-well plate (Falcon cell culture 96-well multi-well plate, with flat bottom lid) coated with 0.1 mg/ml collagen type 1 (Sigma-Aldrich), and cultured at 37° C. for 24 hours with 5% $CO_2$ using Endothelial Cell Growth Medium (PromoCell, Germany). Bismuth citrate, bismuth subnitrate, bismuth tartrate, or zinc sulfate dissolved in saline, and hydrogen peroxide at a final concentration of 450 µM were added to the medium and incubated for 6 hours to simultaneously stress the cells and treat them with test compounds. The cell viability after loading stress was measured using PrestoBlue (registered trademark) Cell Viability Reagent (Life Technologies).

Figure 17:
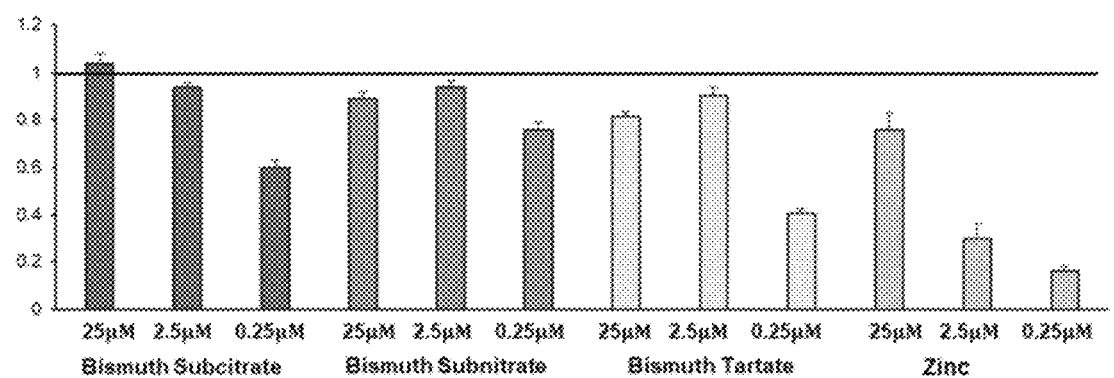
FIG. 17 is a graph of the cell viability of human brain vascular endothelial cells loaded with reactive oxygen species stress in the presence of bismuth subcitrate, bismuth subnitrate, bismuth tartrate, or zinc sulfate.

The cell viability is illustrated in FIG. 17 when the cell viability of the control without hydrogen peroxide stress is 1 and the cell-free is 0. Bismuth subcitrate, bismuth subnitrate, and bismuth tartrate all exhibited a significantly higher cell protective effect on hCMEC/D3 compared with that of zinc sulfate. Note that the survival rate of the cells subjected to hydrogen peroxide stress and not added the test compound was about 0.2. From this result, it was confirmed that the bismuth-containing compound had a protective effect on the brain vascular endothelial cells, and that its effect was stronger than that of zinc, which was a metal known to have a cell protective effect.

The invention claimed is:

1. A method for treating a disease accompanied with a blood brain spinal cord barrier disorder, comprising administering an effective amount of a bismuth-containing compound or a pharmaceutically acceptable salt thereof to a subject in need thereof, wherein the disease accompanied with a blood brain spinal cord barrier disorder is selected from the group consisting of brain injury, spinal cord injury, and compressive myelopathy, and wherein the bismuth-containing compound is selected from the group consisting of bismuth subnitrate, bismuth subcitrate, and bismuth tartrate.

2. The method according to claim 1, wherein the disease is brain injury.

3. The method according to claim 1, wherein the disease is spinal cord injury.

4. The method according to claim 1, wherein the disease is compressive myelopathy.

5. The method according to claim 1, wherein the bismuth-containing compound is bismuth subnitrate.

6. A method for treating a disease, comprising administering an effective amount of a bismuth-containing compound or a pharmaceutically acceptable salt thereof to a subject in need thereof, wherein the disease is selected from the group consisting of brain injury, spinal cord injury, and compressive myelopathy, wherein the bismuth-containing compound is selected from the group consisting of bismuth subnitrate, bismuth subcitrate, and bismuth tartrate.

7. The method according to claim 6, wherein the disease is brain injury.

8. The method according to claim 6, wherein the disease is spinal cord injury.

9. The method according to claim 6, wherein the disease is compressive myelopathy.

10. The method according to claim 6, wherein the bismuth-containing compound is bismuth subnitrate.

11. The method according to claim 1, wherein the bismuth-containing compound is bismuth subcitrate.

12. The method according to claim 1, wherein the bismuth-containing compound is bismuth tartrate.

13. The method according to claim 6, wherein the bismuth-containing compound is bismuth subcitrate.

14. The method according to claim 6, wherein the bismuth-containing compound is bismuth tartrate.

* * * * *